US010775390B2

(12) United States Patent
Lehman et al.

(10) Patent No.: US 10,775,390 B2
(45) Date of Patent: Sep. 15, 2020

(54) METHODS AND MATERIALS FOR IDENTIFYING AND TREATING ACUTE GRAFT-VERSUS-HOST DISEASE

(71) Applicant: Mayo Foundation for Medical Education and Research, Rochester, MN (US)

(72) Inventors: Julia S. Lehman, Rochester, MN (US); Alexander Meves, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/477,073

(22) PCT Filed: Jan. 12, 2018

(86) PCT No.: PCT/US2018/013520
§ 371 (c)(1),
(2) Date: Jul. 10, 2019

(87) PCT Pub. No.: WO2018/132673
PCT Pub. Date: Jul. 19, 2018

(65) Prior Publication Data
US 2019/0339290 A1    Nov. 7, 2019

Related U.S. Application Data

(60) Provisional application No. 62/445,945, filed on Jan. 13, 2017.

(51) Int. Cl.
*A61K 31/565* (2006.01)
*A61K 31/56* (2006.01)
*G01N 33/68* (2006.01)
*A61P 37/06* (2006.01)

(52) U.S. Cl.
CPC ......... *G01N 33/6893* (2013.01); *A61K 31/56* (2013.01); *A61P 37/06* (2018.01); *G01N 2800/245* (2013.01)

(58) Field of Classification Search
CPC .............................. A61K 31/565; A61K 31/56
USPC .................................. 514/171, 177, 178, 182
See application file for complete search history.

(56) References Cited

U.S. PATENT DOCUMENTS

| 6,200,559 B1 | 3/2001 | Wussow | |
| 2009/0186017 A1* | 7/2009 | Shibuya | A61K 39/3955 424/132.1 |

OTHER PUBLICATIONS

Malard et al., "Increased Plamacytoid Dendritic Cells and Rod-Expressing Immune Effectors in Cutaneous Acute Graft-Versus-Host Disease", Journal of Leukocyte Biology, 2013, vol. 94, No. 6, pp. 1337-1343. (Year: 2013).*
Ackermann et al., "The vertebrate homologue of sulfide-quinone reductase in mammalian mitochondria," Cell Tissue Res., 358(3):779-92, Dec. 2014.
Balasubramanian et al., "The interferon-induced GTPase, mGBP-2, confers resistance to paclitaxel-induced cytotoxicity without inhibiting multinucleation," Cell Mol. Biol., 52(1):43-9, May 2006 (Abstract).
Batra et al., "Autologous Graft versus Host Disease: An Emerging Complication in Patients with Multiple Myeloma," Bone Marrow Res., 2014:891427, 2014.
Briggs et al., "Cloning and expression 419 of the human myeloid cell nuclear differentiation antigen: regulation by interferon alpha," J. Cell Biochem., 49(1):82-92, May 1992.
Briggs et al., "The human myeloid cell nuclear differentiation antigen gene is one of at least two related interferon-inducible genes located on chromosome 1q that are expressed specifically in hematopoietic cells," Blood, 83(8):2153-62, Apr. 1994.
Budde et al., "Prediction of graft-versus-host disease: a biomarker panel based on lymphocytes and cytokines," Ann. Hematol., 96(7):1127-33, Jul. 2017.
Bullard et al., "Evaluation of statistical methods for normalization and differential expression in mRNA-Seq experiments," BMC Bioinformatics, 11(1):94, Feb. 2010.
Cavet et al., "Interferon-gamma and interleukin-6 gene polymorphisms associate with graft-versus-host disease in HLA-matched sibling bone marrow transplantation," Blood, 98(5):1594-600, Sep. 2001.
Copelan, "Hematopoietic stem-cell transplantation," N. Engl. J. Med., 354(17):1813-26, Apr. 2006.
Cromvik et al., Eosinophils in the blood of hematopoietic stem cell transplanted patients are activated and have different molecular marker profiles in acute and chronic graft-versus-host disease. Immun. Inflamm. Dis., 2(2):99-113, Aug. 2014.
Diener et al., "MicroRNA expression profiles of serum from patients before and after chemotherapy," Genom. Data, 6:125-7, Dec. 2015.
Drobyski et al., "Severe autologous GVHD after hematopoietic progenitor cell transplantation for multiple myeloma," Bone Marrow Transplant., 43(2):169-77, Jan. 2009.
Ferrara et al., "The Pathophysiology of Acute Graft-versus-Host Disease," Int. J. Hematol., 78(3):181-7, Oct. 2003.
Fidler et al. Spontaneous graft versus host disease occurring in a patient with multiple myeloma after autologous stem cell transplant, Am. J. Hematol., 87(2):219-21, Feb. 2012.
Fiema et al., High throughput sequential ELISA for validation of biomarkers of acute graft-versus-host disease, J. Vis. Exp., 68:4247, Oct. 2012.
Giffin et al., "Modulation of Kaposi's sarcoma-associated herpesvirus interleukin-6 function by hypoxia-upregulated protein 1," J. Virol., 88(16):9429-41, Aug. 2014.
Gilliam and, Murphy, "Cellular pathology of cutaneous graft-versus-host disease," Ferrara JLM DH, Burakoff SJ, editors. New York: Marcel Dekker, Inc.; Graft-Versus-Host Disease, Ed 2, Revised and Expanded. 1997, 291-314.
Giralt et al, "Phase I trial of cyclosporine-induced autologous graft-versus-host disease in patients with multiple myeloma undergoing high-dose chemotherapy with autologous stem-cell rescue," J. Clin. Oncol., 15(2):667-73, Feb. 1997.

(Continued)

*Primary Examiner* — Raymond J Henley, III
(74) *Attorney, Agent, or Firm* — Fish & Richardson P.C.

(57) ABSTRACT

This document provides methods and materials involved in identifying and/or treating acute GVHD. For example, methods and materials for detecting elevated levels of nucleic acid expression (e.g., an elevated level of MxA nucleic acid expression or an elevated level of expression of a nucleic acid that encodes a polypeptide listed in Table 2, Table 3, and/or Table 4) in a skin sample to identify a mammal as having acute GVHD are provided.

9 Claims, 1 Drawing Sheet

(56) References Cited

OTHER PUBLICATIONS

Goddard et al., "A case of severe cutaneous, GI and liver GVHD in a patient with multiple myeloma, status-post-second auto-SCT," Bone Marrow Transplant., 45:409-11, Feb. 2010.
Graham et al., "Hepatic adenomas with synchronous or metachronous fibrolamellar carcinomas: both are characterized by LFABP loss," Mod. Pathol., 29(6):607-15, Mar. 2016.
Heidegger et al., "The role of pattern-recognition receptors in graft-versus-host disease and graft-versus-leukemia after allogeneic stem cell transplantation," Front. Immunol., 5:337, Jul. 2014.
Holler et al., "Metagenomic analysis of the stool microbiome in patients receiving allogeneic stem cell transplantation: loss of diversity is associated with use of systemic antibiotics and more pronounced in gastrointestinal graft-versus-host disease," Biol. Blood Marrow Transplant., 20(5):640-5, May 2014.
Hood et al., "Acute graft-vs-host disease. Development following autologous and syngeneic bone marrow transplantation," Arch. Dermatol., 123(6):745-50, Jun. 1987.
Jacobsohn et al., "Acute graft versus host disease," Orphanet J. Rare Dis., 2(1):35: Sep. 2007.
Joly et al., "The HSP90 inhibitor, 17AAG, protects the intestinal stem cell niche and inhibits graft versus host disease development," Oncogene, 35(22):2842-51, Sep. 2016.
Kalari et al. "MAP-RSeq: Mayo Analysis Pipeline for RNA sequencing," BMC Bioinformatics, 15(1):224, Jun. 2014.
Karaköse et al., "The focal adhesion protein PINCH-1 associates with EPLIN at integrin adhesion sites," J. Cell Sci., 128(5):1023-33, Mar. 2015.
Kittanamongkolchai et al., "Graft-versus host disease in autologous stem cell transplantation: critical care for critical condition," Am. J. Emerg. Med., 31(4):748-9, 2013.
Kline et al., Autologous graft-versus-host disease: harnessing anti-tumor immunity through impaired self-tolerance. Bone Marrow Transplant 41(6):505-13, Nov. 2008.
Koreth et al., "Bortezomib, tacrolimus, and methotrexate for prophylaxis of graft-versus-host disease after reduced-intensity conditioning allogeneic stem cell transplantation from HLA-mismatched unrelated donors," Blood, 114(18):3956-9, Aug. 2009.
Koreth et al., "Bortezomib-based regimen offers promising survival and graft-versus-host disease prophylaxis in myeloablative HLA-mismatched and unrelated donor transplantation: a phase II trial," Biol. Blood Marrow Transplant., 21(11):1907-13, Nov. 2015.
Kutz et al., "Evidence for a functional vasodilatatory role for hydrogen sulphide in the human cutaneous microvasculature," J. Physiol., 593(9):2121-9, May 2015.
Lazarus et al., "Spontaneous autologous graft-versus-host disease in plasma cell myeloma autograft recipients: flow cytometric analysis of hematopoietic progenitor cell grafts," Biol. Blood Marrow Transplant., 17(7):970-8, Jul. 2011.
Lee et al., :Skin graft-versus-host disease following autologous stem cell transplantation for multiple myeloma, Immune Netw., 13:107-10, Jun. 2013.
Levine et al., "A prognostic score for acute graft-versus-host disease based on biomarkers: a multicenter study," Lancet Haematol., 2(1): e21-9, Jan. 2015.
Levine et al., "Acute graft-versus-host disease biomarkers measured during therapy can predict treatment outcomes: a Blood and Marrow Transplant Clinical Trials Network study," Blood, 119(16):3854-60, Apr. 2012.
Levine et al., "Improved accuracy of acute graft-versus-host disease staging among multiple center," Best Pract. Res. Clin. Haematol., 27(3-4):283-7, Sep.-Dec. 2014.
Li et al., "Comparative shotgun proteomics using spectral count data and quasi-likelihood modeling," J. Proteome Res., 9(8):4295-305, Aug. 2010.
Liang et al., "Beta2 integrins separate graft-versus-host disease and graft-versus-leukemia effects," Blood, 111(2):954-62, Jan. 2008.

Ma et al., "IDPicker 2.0: Improved protein assembly with high discrimination peptide identification filtering," J. Proteome Res., 8(8):3872-81, Aug. 2009.
Malard et al., "Increased Plasmacytoid Dendritic Cells and Rort-Expressing Immune Effectors in Cutaneous Acute Graft-Versus-Host Disease," J. Leukocyte Biol., 94(6):1337-43, Aug. 2013.
Mazzone and Ricevuti, "Leukocyte CD11/CD18 integrins: biological and clinical relevance," Haematologica, 80(2):161-7, Mar.-Apr. 1995.
Merighi et al., "Hydrogen sulfide modulates the release of nitric oxide and VEGF in human keratinocytes," Pharmacol. Res., 66(5):428-36, Nov. 2012.
Meves et al., "Tumor Cell Adhesion As a Risk Factor for Sentinel Lymph Node Metastasis in Primary Cutaneous Melanoma," J. Clin. Oncol., 33(23):2509-15, Aug. 2015.
Min et al., "Composite biomarker panel for prediction of severity and diagnosis of acute GVHD with T-cell-depleted allogeneic stem cell transplants-single centre pilot study," J. Clin. Pathol., 70(10):886-90, Oct. 2017.
Mirza et al., "Soluble heat shock protein 70 members in patients undergoing allogeneic hematopoietic cell transplantation," Transpl. Immunol., 36:25-31, May 2016.
Miura et al., "Characterization of the T-cell repertoire in graft-versus-host disease: evidence for the involvement of antigen-driven T-cell response in the development of autologous GVHD," Blood, 98:868-76, Aug. 2001.
Miura et al., "Cytokine 401 and chemokine profiles in autologous graft-versus-host disease (GVHD): interleukin 10 and interferon gamma may be critical mediators for the development of autologous GVHD," Blood, 100(7):2650-8, Oct. 2002.
Miura et al., "Induction of autologous graft versus-host disease with cyclosporine A after peripheral blood stem cell transplantation: analysis of factors affecting induction," J. Allergy Clin. Immunol., 106(1):551-57, Jul. 2000.
Molad et al., "Intravascular neutrophil activation in systemic lupus erythematosus (SLE): dissociation between increased expression of CD11b/CD18 and diminished expression of L-selectin on neutrophils from patients with active SLE," Clin. Immunol. Immunopathol., 71(3):281-6, Jun. 1994.
Oosten et al., "TAP-inhibiting proteins US6, ICP47 and UL49.5 differentially affect minor and major histocompatibility antigen-specific recognition by cytotoxic T lymphocytes," Int. Immunol., 19(9):1115-22, Sep. 2007.
Otegbeye et al., "Autologous GVHD?," Bone Marrow Transplant. ,49(11):1349-51, Nov. 2014.
Paczesny et al., "Elafin is a biomarker of graft-versus-host disease of the skin," Sci. Transl. Med., 2(13):13ra2, Jan. 2010.
Pai et al., "Therapeutic benefit of bortezomib on acute graft-versus-host disease is tissue specific and is associated with interleukin-6 levels," Biol. Blood Marrow Transplant., 20(2):1899-904, Dec. 2014.
PCT International Preliminary Report on Patentability in International Appln. No. PCT/US2018/013520 dated Jul. 25, 2019, 8 pages.
PCT International Search Report and Written Opinion in International Appln. No. PCT/US2018/013520 dated Apr. 26, 2018, 11 pages.
Ratanatharathorn et al., "Phase III Study Comparing Methotrexate and Tacrolimus (Prograf, FK506) With Methotrexate and Cyclosporine for Graft-Versus-Host Disease Prophylaxis After HLA-Identical Sibling Bone Marrow Transplantation," Blood, 92(7):2303-14, Oct. 1998.
Renteria et al., "Development of a biomarker scoring system for use in graft versus-host disease," Biomark Med., 10(8):793-5, Jul. 2016.
Reyes and Klimpel, "Interferon alpha/beta synthesis during acute graft-versus-host disease," Transplantation, 43(3):412-6, Mar. 1987.
Robinson et al., "edgeR: a Bioconductor package for differential expression analysis of digital gene expression data," Bioinformatics, 26(1):139-40, Jan. 2010.
Roddy et al., "Tocilizumab for steroid refractory acute graft-versus-host disease," Leukemia Lymphoma, 57(1):81-5, 2015.

(56) References Cited

OTHER PUBLICATIONS

Staeheli and Sutcliffe, "Identification of a second interferon-regulated murine Mx gene," Mol. Cell Biol., 8(10):4524-8, Oct. 1988.

Sugerman et al., "Kinetics of gene expression in murine cutaneous graft-versus-host disease," Am. J. Pathol., 164(6):2189-202, Jun. 2004.

Sun et al., "Differential effects of proteasome inhibition by bortezomib on murine acute graft-versus host disease (GVHD): delayed administration of bortezomib results in increased GVHD438 dependent gastrointestinal toxicity," Blood, 106(9):3293-9, Nov. 2005.

Tabb et al., "MyriMatch: highly accurate tandem mass spectral peptide identification by multivariate hypergeometric analysis," J. Proteome Res., 6(2):654-61, Feb. 2007.

Wang and Yang, "The complex and central role of interferon-gamma in graft-versus-host disease and graft-versus-tumor activity," Immunol. Rev., 258(1): 30-4, Feb. 2014.

Wang et al., "Hydrogen sulfide accelerates wound healing in diabetic rats," Int. J. Clin. Exp. Pathol., 8(5):5097-104, May 2015.

Wang et al., "The protective effect of hydrogen sulfide on systemic sclerosis associated skin and lung fibrosis in mice model," Springerplus, 5(1):1084, Jul. 2016.

Whangbo et al., "Antibiotic-mediated modification of the intestinal microbiome in allogeneic hematopoietic stem cell transplantation," Bone Marrow Transplant., 52(2):183-90, Aug. 2016.

Yoshimasu et al., "MxA expression in patients with viral infection after allogeneic stem cell transplantation," Bone Marrow Transplant., 32(3):313-6, Aug. 2003.

Zalom et al., "Autologous graft-versus-host disease after denileukin diftitox and autologous stem cell transplantation for refractory T-cell lymphoma," Leukemia Lymphoma, 50(1):124-6, Jan. 2009.

Zhang et al., "Proteomic parsimony through bipartite graph analysis improves accuracy and transparency," J. Proteome Res., 6(9):3549-57, Sep. 2007.

Zhao et al., "IL-22 promoted CD3+T cell infiltration by IL-22R induced STAT3 phosphorylation in murine acute graft versus host disease target organs after allogeneic bone marrow transplantation," Int. Immunopharmacol., 39:383-8. 2016.

Zhu et al., "Cytotoxic T Lymphocyte Antigen-4 Down-Regulates T Helper 1 Cells by Increasing Expression of Signal Transducer and Activator of Transcription 3 in Acute Graft-versus-Host Disease," Biol. Blood Marrow Transplant., 22(2):212-9, Feb. 2016.

* cited by examiner

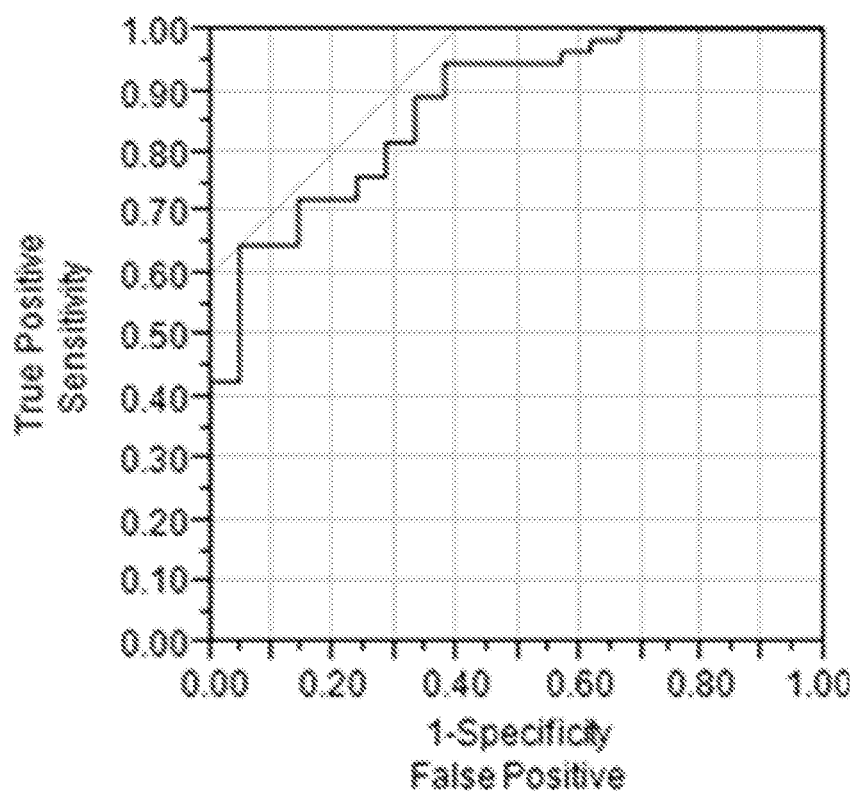

METHODS AND MATERIALS FOR IDENTIFYING AND TREATING ACUTE GRAFT-VERSUS-HOST DISEASE

CROSS-REFERENCE TO RELATED APPLICATIONS

This application is a National Stage application under 35 U.S.C. § 371 of International Application No. PCT/US2018/013520, having an International Filing Date of Jan. 12, 2018, which claims the benefit of U.S. Patent Application Ser. No. 62/445,945, filed on Jan. 13, 2017. The disclosures of the prior applications are considered part of (and are incorporated by reference in) the disclosure of this application.

BACKGROUND

1. Technical Field

This document relates to methods and materials involved in identifying and treating acute graft-versus-host disease. For example, this document provides methods and materials for detecting elevated levels of nucleic acid expression (e.g., an elevated level of MxA nucleic acid expression) in a skin sample to identify a mammal as having acute graft-versus-host disease (GVHD). Once detected as having acute graft-versus-host disease, the mammal can be administered a treatment agent (e.g., a systemic corticosteroid) to treat acute graft-versus-host disease without a concern of worsening a viral infection within the mammal.

2. Background Information

Hematopoietic cell transplantation (HCT) is a potentially curative treatment for patients with certain hematologic malignancies, genetic diseases, immunodeficiency syndromes and hemoglobinopathies. Acute GVHD, a serious complication of HCT, may affect the skin, gastrointestinal system, liver, and other organs. The skin is affected in acute GVHD in approximately 70% of patients (Ratanatharathom et al., *Blood.* 92(7):2303 (1998)). The pathogenesis of acute cutaneous GVHD is immunologically complicated. The fundamental principles of pathogenesis include recognition of host cells as being foreign cells, and the development of an immunologic effect against infused cells that spills over to involve target organs, with resultant damage to the affected organs. Interferon mediated cytokines in particular are implicated in the early pathogenesis of GVHD. There is also increasing recognition of the importance of the target organ microbiome in the development of GVHD, something that has been studied primarily in the gastrointestinal system.

Researchers have evaluated the kinetics of genetic expression profiles of acute GVHD in the skin of murine allogeneic GVHD (allo-GVHD) models (Sugerman et al., *Am J Pathol.* 164(6):2189-202 (2004)). In this other study, investigators discovered that genes upregulated in acute GVHD in the skin tended to be those that are interferon-induced, are involved in antigen presentation, function in cellular adhesion, or are acute-phase reactants, all roles that are part of the working pathogenetic hypotheses of acute GVHD. However, little is known about the molecular profiles of acute GVHD in human skin.

SUMMARY

Assessing the molecular profiles of affected tissue (e.g., skin) rather than serum has the advantage of signal concentration. Since the skin is frequently affected in acute GVHD, readily visualized, and biopsied with minimal risk to the patient, the skin is an attractive tissue to evaluate in the diagnosis of acute GVHD.

This document provides methods and materials involved in identifying and treating GVHD (e.g., acute GVHD). For example, this document provides methods and materials for detecting elevated levels of nucleic acid expression (e.g., an elevated level of MxA nucleic acid expression or an elevated level of expression of a nucleic acid that encodes a polypeptide listed in Table 2, Table 3, and/or Table 4) in a skin sample to identify a mammal as having acute GVHD. Using the methods and materials provided herein can allow clinicians to identify GVHD at an early stage (or later), thereby allowing for early and effective treatment of GVHD. Once detected as having acute GVHD at an early stage, the mammal can be administered a treatment agent (e.g., a systemic corticosteroid) to treat acute GVHD at a time that has an increased chance of being effective. In some cases, the methods and materials provided herein can be used to treat GVHD without a concern that the mammal has a different medical condition other than GVHD (e.g., a viral infection) that might become worse upon administration of a GVHD treatment agent (e.g., a corticosteroid).

As described herein, mammals (e.g., humans) identified as having skin cells having an elevated level of a polypeptide list in Table 2, Table 3, and/or Table 4 can be identified as having acute GVHD. In some cases, mammals (e.g., humans) identified as having skin cells having an elevated level of a polypeptide list in Table 2, Table 3, and/or Table 4 can be identified as having acute GVHD and effectively treated with one or more systemic agents (such as tacrolimus, mycophenolate mofetil, intravenous immunoglobulin, extracorporeal photophoresis, TNF-alpha inhibitors, and IL-17 inhibitors) or topical agents (such as topical steroids or calcineurin inhibitors).

This document also provides methods for identifying a mammal (e.g., a human) as having GVHD (e.g., acute GVHD). For example, skin cells obtained from a mammal that received HCT can be assessed to determine if they express an elevated level of one or more of the polypeptides listed in Table 2, Table 3, and/or Table 4. If the skin cells have an elevated level of one or more of the polypeptides listed in Table 2, Table 3, and/or Table 4, then the mammal can be classified as having acute GVHD. If the skin cells do not have an elevated level of one or more of the polypeptides listed in Table 2, Table 3, and/or Table 4, then the mammal can be classified as not having acute GVHD. In some cases, mammals lacking skin cells having an elevated level of one or more of the polypeptides listed in Table 2, Table 3, and/or Table 4 can be classified as having a medical condition other than GVHD such as a viral infection (e.g., a cytomegalovirus infection) and/or a rash (e.g., a medication rash such as a vacuolar interface drug reaction).

In general, one aspect of this document features a method for treating acute GVHD in a mammal. The method includes, or consists essentially of, identifying a mammal as having skin cells having an elevated level of a polypeptide listed in Table 2, Table 3, and/or Table 4, and administering a corticosteroid to said mammal under conditions where the severity of the acute GVHD within the mammal is reduced. The mammal can be a human. The acute GVHD can be acute allo-GVHD. The skin cells can have an elevated level of interferon-induced GTP-binding protein Mx1, interferon-induced GTP binding protein Mx2, interferon-induced guanylate binding protein, or myeloid cell nuclear differentiation antigen. The skin cells can have an elevated level of antigen peptide transporter 1, signal transducer and activator of transcription 3, or proteasome subunit alpha type-3 isoform 1. The skin cells can have an elevated level of integrin B2 precursor or LIM domain and actin-binding protein 1. The skin cells can have an elevated level of heat shock protein 105 kDa, hypoxia-induced peptide, or mitochondrial sulfide:quinone oxidoreductase.

In another aspect, this document features a method for identifying a mammal as having acute GVHD. The method includes, or consists essentially of, detecting the presence of skin cells having an elevated level of a polypeptide listed in Table 2, Table 3, and/or Table 4, and classifying the mammal as having acute GVHD. The mammal can be a human. The acute GVHD can be acute allo-GVHD. The skin cells can have an elevated level of interferon-induced GTP-binding protein Mx1, interferon-induced GTP binding protein Mx2, interferon-induced guanylate binding protein, or myeloid cell nuclear differentiation antigen. The skin cells can have an elevated level of antigen peptide transporter 1, signal transducer and activator of transcription 3, or proteasome subunit alpha type-3 isoform 1. The skin cells can have an elevated level of integrin B2 precursor or LIM domain and actin-binding protein 1. The skin cells can have an elevated level of heat shock protein 105 kDa, hypoxia-induced peptide, or mitochondrial sulfide:quinone oxidoreductase.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

FIG. 1 shows a receiver operating characteristic (ROC) curve for diagnosis of acute GVHD (vs. medication reaction) of the skin. The area under the curve was 0.87.

DETAILED DESCRIPTION

This document provides methods and materials for identifying and/or treating GVHD (e.g., acute GVHD). For example, this document provides methods and materials for identifying a mammal as having skin cells and/or skin tissues having an elevated level of one or more of the polypeptides listed in Table 2, Table 3, and/or Table 4 and administering one or more GVHD treatment agents to treat the identified mammal. In some cases, a mammal (e.g., a human) can be identified as having skin cells and/or skin tissues having an elevated level of one or more of the polypeptides listed in Table 2, Table 3, and/or Table 4 as described herein and classified as having acute GVHD based, at least in part, on the presence of such skin cells and/or skin tissues.

Any appropriate mammal can be identified as having GVHD (e.g., acute GVHD) and/or treated for GVHD (e.g., acute GVHD) as described herein. For example, humans and other primates such as monkeys can be identified as having skin cells and/or skin tissues having an elevated level of one or more of the polypeptides listed in Table 2, Table 3, and/or Table 4 and treated with one or more GVHD treatment agents. In some cases, dogs, cats, horses, cows, pigs, sheep, mice, and rats can be identified and treated as described herein.

Any appropriate GVHD can be identified as described herein. GVHD can be acute GVHD or chronic GVHD. For example, acute allo-GVHD or autologous GVHD (auto-GVHD) can be identified based, at least in part, on the presence of skin cells and/or skin tissues having an elevated level of one or more of the polypeptides listed in Table 2, Table 3, and/or Table 4 and treated with one or more GVHD treatment agents as described herein.

Any appropriate sample can be assessed to identify cells and/or tissues (e.g., skin cells and/or skin tissues) as having an elevated level of one or more of the polypeptides listed in Table 2, Table 3, and/or Table 4. For example, biological samples such as tissue samples (e.g., skin, gastrointestinal system, or liver tissue) can be obtained from a mammal and assessed for the presence of an elevated level of one or more of the polypeptides listed in Table 2, Table 3, and/or Table 4. For example, biological biopsies such as tissue biopsies (e.g., skin, gastrointestinal system, or liver biopsies) can be obtained from a mammal and assessed for the presence of an elevated level of one or more of the polypeptides listed in Table 2, Table 3, and/or Table 4.

Any appropriate method can be used to identify cells and/or tissues (e.g., skin cells and/or skin tissues) as having an elevated level of one or more of the polypeptides listed in Table 2, Table 3, and/or Table 4. For example, mRNA-based assays such as RT-PCR can be used to identify skin cells and/or skin tissues as having an elevated level of mRNA encoding a polypeptide listed in Table 2, Table 3, and/or Table 4. In some cases, polypeptide-based assays such as antibody staining techniques or ELISAs using antibodies can be performed to detect the presence of skin cells and/or skin tissues having an elevated level of one or more of the polypeptides listed in Table 2, Table 3, and/or Table 4.

The term "elevated level" as used herein with respect to polypeptide expression refers to a level of one or more polypeptides in cells and/or tissues (e.g., skin cells and/or skin tissues) that is greater (e.g., at least 5, 10, 25, 35, 45, 50, 55, 65, 75, 80, 90, or 100 percent greater) than the median expression level of that polypeptide by a random sampling of 5, 10, 15, 20, 30, 40, 50, 100, 500, or more comparable cell samples (e.g., skin cell samples and/or skin tissue samples) from comparable mammals (e.g., humans) known not to have GVHD. In some cases, an elevated level of polypeptides can be expressed by skin cells. In some cases, an elevated level of polypeptides can be expressed by another cell type and absorbed by skin cells and/or skin tissue.

Once identified as having cells and/or tissues (e.g., skin cells and/or skin tissues) having an elevated level of one or more of the polypeptides listed in Table 2, Table 3, and/or Table 4, the mammal can be administered or instructed to self-administer one or more GVHD treatment agents to reduce the severity of GVHD within the mammal. In some cases, reducing the severity of GVHD in a mammal can include reducing or eliminating one or more symptoms of GVHD (e.g., skin rashes, immune-mediated pneumonitis, intestinal inflammation, sloughing of the intestinal mucosal membrane, severe diarrhea, abdominal pain, nausea, vomiting, and/or elevated bilirubin levels). In some cases, reducing the severity of GVHD in a mammal can include reducing the stage of GVHD. The stage of GVHD can be evaluated as described elsewhere (see, e.g., Jacobsohn et al., *Orphanet J Rare Dis* 2007; 2:35). A GVHD treatment agent can be any appropriate GVHD treatment agent. Examples of GVHD treatment agents include, without limitation, systemic steroids (e.g., corticosteroids), systemic calcineurin inhibitors, systemic biologic agents, extracorporeal photophoresis, intravenous immunoglobulin, topical steroids, and topical calcineurin inhibitors. In some cases, GVHD treatment agents can be as described elsewhere (see, e.g., Jacobsohn et al., *Orphanet J Rare Dis* 2007; 2:35). In some cases, one or more GVHD treatment agents can be selected according to clinical features of a mammal (see, e.g. Min et al., *J Clin Pathol.* 2017 October; 70(10):886-890; and Budde et al., *Ann Hematol.* 2017 July; 96(7):1127-1133). In some cases, two or more GVHD treatment agents (e.g., two, three, four, five, or more GVHD treatment agents) can be administered to a mammal to reduce the severity of GVHD within the mammal.

In some cases, one or more GVHD treatment agents can be administered to a mammal once or multiple times over a period of time ranging from days to weeks. In some cases, one or more GVHD treatment agents can be formulated into a pharmaceutically acceptable composition for administration to a mammal having GVHD. For example, a therapeutically effective amount of a GVHD treatment agent (e.g., a steroid) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more GVHD treatment agents can be designed for oral, parenteral (including subcutaneous, intramuscular, intravenous, and intradermal), or topical administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets. Topical medications can be formulated as solutions, creams, ointments, gels or aerosolized sprays.

In some cases, a pharmaceutically acceptable composition including one or more GVHD treatment agents can be administered locally or systemically. For example, a composition provided herein can be administered locally by injection into subcutaneous tissue. In some cases, a composition provided herein can be administered systemically, orally, or by injection to a mammal (e.g., a human).

Effective doses can vary depending on the severity of the GVHD, the route of administration, the age and general health condition of the subject, excipient usage, the possibility of co-usage with other therapeutic treatments such as use of other agents, and the judgment of the treating physician.

An effective amount of a composition containing one or more GVHD treatment agents can be any amount that reduces the severity of GVHD within the mammal without producing significant toxicity to the mammal. For example, an effective amount of a GVHD treatment agent such as prednisone can be from about 10 mg per day to about 80 mg per day (e.g., by oral administration). In some cases, between about 10 mg per day mg and about 80 mg per day of a GVHD treatment agent can be administered to an average sized human (e.g., about 75-85 kg human).

If a particular mammal fails to respond to a particular amount, then the amount of a GVHD treatment agent can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., GVHD) may require an increase or decrease in the actual effective amount administered.

The frequency of administration of a GVHD treatment agent can be any amount that reduces the severity of GVHD within the mammal without producing significant toxicity to the mammal. For example, the frequency of administration of a GVHD treatment agent can be from about once daily to about once every six months. The frequency of administration of a GVHD treatment agent can remain constant or can be variable during the duration of treatment. A course of treatment with a composition containing a GVHD treatment agent can include rest periods. For example, a composition containing one or more GVHD treatment agents can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., GVHD) may require an increase or decrease in administration frequency.

An effective duration for administering a composition containing one or more GVHD treatment agents can be any duration that reduces the severity of GVHD within the mammal without producing significant toxicity to the mammal. In some cases, the effective duration can vary from several days to several weeks. In general, the effective duration for reducing the severity of GVHD within the mammal can range in duration from about 2 weeks to about 12 weeks. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and/or the severity of one or more symptoms related to the condition being treated (e.g., GVHD) can be monitored. Any appropriate method can be used to determine whether or not the severity of GVHD within the mammal is reduced. For example, clinical evaluation, tissue biopsy, and/or blood tests can be used to assess the severity of GVHD within the mammal.

The invention will be further described in the following examples, which do not limit the scope of the invention described in the claims.

EXAMPLES

Example 1—Analysis of Skin in Acute Graft-Versus-Host Disease, Autologous Graft-Versus-Host Disease, and Normal Skin Methods Patients with skin involvement by allo-GVHD or auto-GVHD/auto-GVHD-like syndrome were identified from electronic medical records. The chart of each eligible patient was manually reviewed by at least one board certified dermatologist for appropriateness of inclusion. Only definite cases with compatible clinical features, timing of disease onset, clinical course, and consistent histopathologic changes were included in the study. All patients with archived (formalin-fixed, paraffin embedded) skin biopsies demonstrating auto-GVHD were selected, as identified from the Mayo Clinic BMT/GVHD database and confirmed by a dermatopathologist. Since auto-GVHD tends to be clinically and histopathologically mild, the Mayo Clinic BMT/GVHD database was also searched for an additional six diagnostic skin biopsies from 64 patients with allo-GVHD that had grade 1-2 histopathologic changes in the skin, as confirmed by manual review of slides by a dermatopathologist. Moreover, five control skin specimens from patients who had undergone hematopoietic stem cell transplantation were identified. For the controls, re-excision specimen tips (containing normal skin) or biopsies that had been performed for clinical skin changes but that showed negligible histopathologic changes in the epidermis or dermis were selected. Any skin specimens from patients for whom a clinical diagnosis of GVHD was being strongly considered were excluded. Cases were excluded if skin biopsy tissue blocks were exhausted or unavailable or if too few proteins could be identified with proteomic analysis from any given specimen.

Mass Spectrometry-Based Proteomics

A laser capture microdissection-assisted liquid chromatography-based tandem mass spectrometry (LCM-LC-MS/MS) method modified from methods described elsewhere (Graham et al., *Mod Pathol.* 29(6):607-15 (2016)) were used. In brief, for each case, 10 µm thick sections of formalin-fixed, paraffin-embedded (FFPE) skin specimens were mounted onto polyethylene naphthalate (PEN) membrane slides and stained them with Congo Red stain (Sigma-Aldrich, St. Louis, Mo.) for microanatomic visualization. A board-certified dermatopathologist performed LCM to isolate the epidermis (mid-granular layer to basal layer), the dermal-epidermal junction, and the superficial papillary dermis (to the superficial vascular plexus). A total of 1,000,000 µm$^2$ of tissue was dissected per case using adhesive cap tubes (Zeiss). Proteins in the collected FFPE fragments were extracted and denatured by heating at 98° C. for 1 hour in a buffer composed of 0.1M Tris (pH 8.5) with 0.002% Zwittergent Z3-16. Cysteine-Cysteine disulfide bridges in the extracted proteins were reduced with dithiothreitol (DTT) and alkylated with iodoacetamide.

Proteins were digested into peptides by an overnight incubation with trypsin. Resulting peptide mixture was separated on a 35 cm×100 µm column with an analytical gradient where mobile phase B was increased from 2-40% in 2 hours at a flow rate of 400 nL/minute. A Q-Exactive Plus mass spectrometer (Thermo-Fisher Scientific, Waltham, Mass.) operating in data dependent mode analyzed the eluting peptides by collecting MS1 data at 70000 resolving power (at 200 m/z) and an AGC value of 1E6 over a m/z range of 340-1500. Tandem mass spectra (MS/MS) were collected on the top 20 precursor ions present in each MS1 scan. Precursors were isolated for fragmentation with an AGC value of 1E5, a max ion fill time of 50 ms, and an isolation window of 1.5 Da. Fragment ions for MS/MS were obtained with normalized collision energy of 28 and measured at 17500 resolving power (at 200 m/z). Fragmented precursors were put on an exclusion list for 45 seconds.

Bioinformatics

MS/MS data present in all the data files were matched against a composite protein sequence database using MyriMatch (version 2.1.120) search engine [PMID:17269722]. This database contained protein sequences from the RefSeq database (release 53) sub-selected for human species and also common contaminants. Reversed sequence entries were appended to the database for estimating peptide identification false discovery rates (FDRs). MyriMatch were derived semi-tryptic peptides from the sequence database while searching for carbamidomethylation of cysteine (+57.0125 Da) as static modification. The software also considered the oxidation of methionine, methylation of lysine (+14.0126 Da.), demethylation of lysine (+27.9949 Da.), and formation of N-terminal pyroglutamine (−17.0265 Da) as variable modifications. MyriMatch allowed up to three missed cleavage sites while deriving the peptides and assumed 10 ppm m/z error on both precursor and fragments while performing the peptide spectrum matching. IDPicker (version 3.0.515) filtered the peptide identifications at 2% FDR[PMID: 19522537,17676885]. Filtered peptide identifications were assembled into protein identifications, and protein identifications with at least two distinct peptide identifications were considered for differential expression analysis. QuasiTel software was used to process the spectral count data for identifying differentially expressed proteins between any two experimental groups [PMID:20586475]. To assure consistency and reproducibility of protein identification methods, the auto-GVHD cases were repeated twice, and one of the allo-GVHD cases and one of the negative control cases also were repeated. Moreover, detection of desmoglein 1 (a protein ubiquitously present in the epidermis), collagen XVII (a protein ubiquitously present in the dermal-epidermal basement membrane zone), and collagen VII (a protein ubiquitously present in the superficial dermis) precursor proteins were compared to assess for comparability of tissue collection and processing between groups.

The proteins that were differentially expressed (>20-fold expression; p<0.05; false discovery rate <1%) between each two comparison groups were selected. These protein profiles were compared in each of three groups: auto-GVHD, allo-GVHD, and normal skin control. Statistical significance was achieved when p<0.05.

Results

Three cases of acute auto-GVHD with diagnostic skin biopsies were identified and included. Six cases of allo- GVHD were also studied. One of these was excluded due to identification of too few distinct proteins. Of the 5 cases of normal skin, two were excluded due to identification of insufficient numbers of proteins. The remaining three were skin samples derived for the following indications: Re-excision of atypical nevus (n=1), diffuse skin paresthesias without rash (a definitive cause of which was not found but that self-resolved within a few weeks; n=1), and mild skin redness and swelling (later believed to represent non-specific erythema associated with leg edema; n=1). Clinical features of patients whose specimens were included in the study are outlined in Table 1. Average age of patients in the allo-GVHD, auto-GVHD, and negative control groups were 61.3 years, 34.9 years, and 41.5 years, respectively.

TABLE 1

Clinical and skin histopathologic presentation of patients with auto-GVHD, allo-GVHD or negative control.

| | Allogeneic GVHD | | | | |
|---|---|---|---|---|---|
| Sex | F | M | M | M | F |
| Age at time of biopsy | 36.5 | 31.0 | 41.9 | 37.7 | 27.4 |
| Days after HCT at time of biopsy | 111 | 33 | 33 | 116 | 83 |
| Hematologic diagnosis | AML | PNH | ALL, then therapy-related AML | CML | AML |
| Type of HCT | Allo, MUD | Allo, MRD | Allo, MRD | Allo, MRD | Allo, double umbilical cord blood |
| Conditioning regimen | Fludarabine and busulfan | Cyclophosphamide and ATG | Cyclophosphamide and TBI | Cyclophosphamide and TBI | Fludarabine, cyclophosphamide, TBI |
| GVHD prophylaxis | MTX and tacrolimus | Cyclosporine | Cyclosporine | MTX and cyclosporine | Mycophenolate mofetil and cyclosporine |
| Organs involved by GVHD | Skin | Skin, liver | Skin | Skin | Skin, GI |
| Duration of follow-up after HCT (days) | 1472 | 176 | 3590 | 5586 | 484 |
| Clinical outcome | Deceased (AML relapse) | Deceased (cause not documented) | Alive | Alive | Deceased (AML relapse) |
| Results of CMV testing (blood PCR) at time of rash | Negative | Negative | Negative | Not done | Negative |
| Skin histopathology grade | 2 | 2 | 1 | 2 | 2 |

| | Autologous GVHD | | | Negative controls | | |
|---|---|---|---|---|---|---|
| Sex | F | F | M | M | M | M |
| Age at time of biopsy | 70.1 | 60.5 | 62.1 | 56.3 | 45.5 | 22.8 |
| Days after HCT at time of biopsy | 38 | 142 | 41 | 323 | 791 | 113 |
| Hematologic diagnosis | MM | MM | MM | ALL | CLL | ALL |
| Type of HCT | Auto | Auto | Auto | Allo, MRD | Allo, MRD | Allo, MRD |
| Conditioning regimen | Melphalan | Melphalan | Melphalan | Fludarabine and melphalan | Fludarabin and melphalan | Etoposide and TBI |
| GVHD prophylaxis | None | None | None | MTX and tacrolimus | Cyclosporine | MTX and cyclosporine |
| Organs involved by GVHD | Skin, GI | Skin, GI | Skin, GI | N/A | N/A | N/A |
| Duration of follow-up after HCT (days) | 99 | 22672 | 43 | 1032 | 1018 | 4362 |
| Clinical outcome | Deceased ("failure to thrive") | Deceased (cause not documented) | Deceased (complications of MM) | Alive | Alive | Alive |
| Results of CMV testing (blood PCR) at time of rash | Negative | Negative | Negative | Not done | Not done | Not done |
| Skin histopathology grade | 2 | 1 | 2 | N/A | N/A | N/A |

F = female;
M = male;
MM = multiple myeloma;
CML = chronic myelogenous leukemia;
ALL = acute lymphoblastic leukemia;
AML = acute myeloid leukemia;
PNH = paroxysmal nocturnal hemoglobinuria;
allo = allogeneic;
MUD = matched unrelated donor;
MRD = matched related donor;
GI = gastrointestinal;
NA = not applicable The average number (range) of distinct peptides expressed in the auto-GVHD group was 8,863 (5,822-11,187), in the allo-GVHD group was 8,304 (4,024-11,873), and in the control group was 5,573 (4,350-6,536). Duplicate runs of the same specimen showed comparable results.

20-fold was selected as a cut-off for significant overexpression of proteins, because there was a considerable gap between that and the $\log^2$ fold differences of the next most heavily expressed proteins (5.8-$\log^2$ fold over controls in the allo-GVHD group and 5.4-$\log^2$ fold in the auto-GVHD group). Compared with negative controls, the auto-GVHD group showed significant overexpression (>20 $\log^2$ fold; p<0.05) of 12 proteins, representing approximately 0.13% of all proteins identified (Table 2). Of these 12 proteins, all (100%) were also significantly overexpressed in the allo-GVHD group compared to negative controls. An additional 14 proteins were significantly overexpressed in allo-GVHD, but not in auto-GVHD compared to negative controls, which when combined with the 12 proteins overlapping with the auto-GVHD group, represented approximately 0.31% of all proteins identified. No protein was significantly overexpressed in negative controls compared to either auto-GVHD or allo-GVHD specimens. The number of proteins which showed significantly different expression of at least 1-fold compared to normal skin controls for auto-GVHD cases was 117 proteins and for allo-GVHD cases, 177. In contrast, auto-GVHD cases had only 37 proteins that significantly differed by at least 1 $\log^2$ fold expression with p<0.05 from allo-GVHD, with none of these exceeding a 5 $\log^2$ fold expression. No proteins were substantially under-expressed in allo- or auto-GVHD compared with controls. Of these specimen groups, no significant differences in expression of the control proteins desmoglein 1 precursor, collagen XVII precursor, or collagen VII precursor were identified in allo-GVHD or auto-GVHD vs. normal skin control. No polypeptide was significantly overexpressed in negative controls over allogeneic GVHD or autologous GVHD.

TABLE 2

Name of polypeptides significantly overexpressed (>20 $\log^2$ fold) in skin sample, by specimen type, compared to negative control.

| Protein name | Auto-GVHD $\log^2$ fold-overexpression vs. negative control | Allo-GVHD $\log^2$ fold-overexpression vs. negative control |
|---|---|---|
| interferon-induced GTP-binding protein Mx1 | 30.1 | 29.8 |
| interferon-induced GTP-binding protein Mx2 | 31 | 29.8 |
| interferon-induced guanylate-binding protein 2 | 29.7 | 29.4 |
| myeloid cell nuclear differentiation antigen | 29.8 | 29.1 |
| antigen peptide transporter 1 | 31.1 | 31.3 |
| proteasome subunit alpha type-3 isoform 1 | 32.3 | 30.4 |
| signal transducer and activator of transcription 3 isoform 2 | 31.3 | 29.4 |
| integrin beta-2 (CD18) precursor | 29.7 | 29.4 |
| LIM domain and actin-binding protein 1 isoform 2 | 31.3 | 29 |
| heat shock protein 105 kDa | 29.5 | 29.2 |
| hypoxia up-regulated protein 1 precursor | 32.9 | 29.8 |
| sulfide:quinone oxidoreductase, mitochondrial | 30.9 | 30.2 |

This example is an investigation of tissue-based protein expression profiles of acute allo-GVHD and acute auto-GVHD in human skin compared to normal skin controls. These results demonstrate that all 12 polypeptides that were overexpressed in acute auto-GVHD were also overexpressed in acute allo-GVHD, implying overlap in pathogenesis between these two clinical entities. Each of these 12 polypeptides of interest fell into one of 4 categories: (1) those that are interferon-induced (interferon-induced GTP-binding protein Mx1, interferon-induced GTP binding protein Mx2, interferon-induced guanylate binding protein, and myeloid cell nuclear differentiation antigen), (2) are involved in cellular signaling, antigen processing and presentation (antigen peptide transporter 1, signal transducer and activator of transcription 3, and proteasome subunit alpha type-3 isoform 1), (3) function as adhesion molecules and their ligands (integrin B2 precursor, and LIM domain and actin-binding protein 1), or (4) respond to cellular stress (heat shock protein 105 kDa, hypoxia-induced peptide, and mitochondrial sulfide:quinone oxidoreductase).

The results provided herein demonstrated substantial overlap of polypeptide overexpression between auto-GVHD and allo-GVHD compared to normal skin control, indicating that the immunobiologic milieu of allo-GVHD is similar to that of auto-GVHD, at least in the skin. As outlined in greater detail above, several of the particular proteins identified mutually in allo- and auto-GVHD were induced by interferons, supporting their role in pathogenesis for both processes. It is possible that the polypeptides preferentially expressed in allo-GVHD but not in auto-GVHD may be related to other patient factors, such as TBI or other treatment-related factors.

Most prior molecular investigations of GVHD studied blood samples in humans or blood or tissue samples in murine models of allo-GVHD. The work provided herein investigated proteomic expression in human skin samples, the advantages of which were several-fold. First, the proteomics approach searched for potentially biologically relevant polypeptides in an unbiased fashion. Second, laser-capture microdissection of the microanatomic areas affected by GVHD concentrated signal in a way that was not readily feasible with blood studies. Third, affected skin was visible and accessible for biopsy, therefore potentially being an ideal source of biologic information for the development of tissue-based assays for clinical practice.

Example 2: Assessment of Polypeptide Expression in Acute Graft-Versus-Host Disease of the Skin Compared with Vacuolar Interface Medication Reaction of the Skin On the basis of tissue-based biomarkers that were identified within Example 1 above, an assay for associated genes was developed and tested on skin biopsy specimens from patients with acute graft-versus-host disease. Results were compared to those from patients with vacuolar interface medication reaction of the skin, a condition that clinically and microscopically may mimic acute GVHD. Other serendipitous genes which our laboratory had studied previously in another context (Meves et al., *J Clin Oncol* 2015; 10:33 (23):2509-15).

Methods

Case and Control Selection

The Mayo Clinic BMT/GVHD database was interrogated for skin biopsy specimens from patients receiving HCT within 100 days of the biopsy date that represented GVHD or other inflammatory process. The corresponding patient chart was carefully reviewed, and specimens representing GVHD with a high degree of probability were included as cases. Those representing vacuolar interface drug rash, with supportive clinical timeframe of drug initiation, response to interventions, and histopathology, were selected as controls. Specimens were excluded if insufficient RNA could be extracted for analysis.

PCR Methods

Based on proteins identified in the discovery phase of the experiments, a quantitative RT-PCR-based assay for use with formalin-fixed paraffin-embedded (FFPE) tissue was developed. For the assay, RNA was purified from FFPE skin biopsy specimens (Qiagen), as described elsewhere (see, e.g., Meves et al., J Clin Oncol 2015; 10:33(23):2509-15). Quantitative RT-PCR was performed using the BioMark HD System and dynamic array integrated fluid circuits (Fluidigm). Forty-three specific targets in 32 genes (26 experimental and 6 control genes) were amplified per cDNA (standards, controls and experimental samples). The following cDNA were run per array: standards in triplicates; control cDNA (internal standard); experimental cDNA; the latter two were in duplicates. All cDNA was pre-amplified (TaqMan Preamp Master Mix, Applied Biosystems). Array-based quantitative PCR was with the help of the TaqMan Gene Expression Master Mix (Applied Biosystems). After thermal cycling, raw Ct data for standards was checked for linear amplification. Copy numbers for negative and positive controls were normalized to housekeeping genes. Averaged, normalized gene copy numbers were compared to an internal standard for inter-experiment variation. Data that did not pass both linear amplification and reproducibility checks were discarded. To account for RNA contamination by basal keratinocytes, keratin 14 (KRT14), a basal keratinocyte marker, was quantified. KRT14 copy number was multiplied with a gene specific, per-copy-of-KRT14 contamination factor that was pre-determined by analyzing normal skin. The product of this calculation was used to correct for keratinocyte background.

Bioinformatics

Quantified gene expression was compared between GVHD and vacuolar drug eruption using Wilcox Test, with statistical significance being achieved when p<0.05. To develop a diagnostic model, genes with |Log 2(FC)|<1 and those with tight correlations with other genes were excluded and the receiver operating characteristic (ROC) curve was optimized. Next, all genes were subjected to a variable selection process to identify candidate genes that can potentially differentiate between GVHD and medication reaction. This process created 1000, randomly seeded, logistic regression models, each configured to use a 3-fold cross-validation. The variables with non-zero coefficients in all 1000 models were considered for final model building. During this phase, logistic regression models were generated for all possible combinations of the final variables. All models with no interdependent variables and the best area under the curve (AUC) for differentiating between GVHD and medication reaction were considered for final reporting. This recursive and layered model building allowed us to identify equally well performing gene expression-based classifiers while reducing the likelihood of over-fitting.

Results

Seven proteins tested were found to be significantly differentially expressed (all overexpressed) in GVHD vs. drug rash: MLANA, MNDA, ITGB2, ITGA2, HYOU, and IL-8 (Table 3). Though several others were differentially expressed, these differences did not meet statistical significance (Table 3).

TABLE 3

Parameter estimates of each gene tested, with probability < ChiSq of <0.05 representing statistical significance.

| Term | Estimate | Std Error | ChiSquare | Prob > ChiSq |
| --- | --- | --- | --- | --- |
| Intercept | −8.7274806 | 4.0427052 | 4.66 | 0.0309* |
| MLANA | 0.3528249 | 0.1644246 | 4.60 | 0.0319* |
| MNDA | 1.65663191 | 0.7723804 | 4.60 | 0.0320* |
| THBS2 | −0.4232822 | 0.2390709 | 3.13 | 0.0766 |
| ITGB2 | −1.4624885 | 0.5838598 | 6.27 | 0.0122* |
| LOXL1 | 0.34668663 | 0.2361953 | 2.15 | 0.1422 |
| SPP1 | −0.3107905 | 0.1893168 | 2.69 | 0.1007 |
| ITGA3 | 0.62400304 | 0.3584789 | 3.03 | 0.0817 |
| ITGA2 | 0.5306192 | 0.2445614 | 4.71 | 0.0300* |
| HYOU | 0.37695986 | 0.1801268 | 4.38 | 0.0364* |
| CXCL1 | −0.3683135 | 0.2089292 | 3.11 | 0.0779 |
| IL8 | 0.89732326 | 0.4127966 | 4.73 | 0.0297* |

Model optimization yielded an ROC curve with an AUC of 0.87 (FIG. 1).

This work represents the novel development of a preliminary tissue-based diagnostic biomarker assay of acute GVHD of the skin. PCR confirmed the differential expression of several of the corresponding genes in GVHD vs. non-GVHD vacuolar interface rash. A simple diagnostic algorithm by quantitative RT-PCR was developed and optimized to aide in differentiation between GVHD and vacuolar interface drug reaction, a challenging distinction of considerable clinical importance.

Example 3. Identification of Additional Potential Tissue-Based Biomarkers of Acute GVHD Methods
RNA Sequencing (RNA-Seq)

RNAseq was performed on skin specimens from patients with acute GVHD or patients with medication reaction following HCT using previously established methods (Meves et al., J Clin Oncol 2015; 10:33(23):2509-15). Briefly, NuGen Ovation RNAseq RNA-derived cDNA libraries (Life Technologies, Grand Island, N.Y.) were used for formalin-fixed, paraffin-embedded tissue. An Agilent Bioanalyzer DNA 1000 chip and Qubit fluorometry (Life Technologies) were used to determine the concentration and size distribution of the resulting libraries. Unique indexes were incorporated at the adaptor ligation phase for three-plex sample loading. Libraries were loaded onto paired end flow cells to generate cluster densities of 700,000/mm$^2$ following Illumina's (San Diego, Calif.) standard protocol. The flow cells were sequenced as 51×2 paired end reads on an Illumina HiSeq 2000. The samples were processed through the Mayo RNA-Seq analysis pipeline, MAP-RSeq (see, e.g., Kalari et al., BMC Bioinformatics 15:224, 2014). Raw and normalized (read per kilobase of gene per million mapped reads) gene expression read counts were obtained per sample. Differential gene expression analysis was carried out using the freely available edgeR (Robinson et al., Bioinformatics 26:139-140, 2010) bioconductor software package (bioconductor.org). Because scaling by total lane counts can bias estimates of differential expression, edgeR uses trimmed mean normalization on raw read counts to determine whether genes are differentially expressed (see, e.g., Bullard J H, et al., BMC Bioinformatics 11:94, 2010) using the negative binomial method. The Benjamini and Hochberg correction was used to control for multiple testing to obtain a false discovery rate of less than 0.05.

Results

Polypeptides differentially expressed in skin biopsies of acute GVHD vs. medication reaction are listed in Table 4.

TABLE 4

Polypeptides differentially expressed in acute GVHD vs. medication reaction in the skin.

| Gene symbol | GVHD vs. drug fold change | GVHD vs. drug p-value | GVHD vs. drug false discovery rate |
|---|---|---|---|
| GSTM5 | −1.962384565 | 5.46E−05 | 0.038074692 |
| IVL | 1.682190352 | 2.00E−05 | 0.022986473 |
| ADARB2 | 6.430711439 | 1.15E−06 | 0.002987662 |
| RP11-106M7.1 | 2.420438182 | 9.83E−05 | 0.047137392 |
| CREB3L1 | −1.919054848 | 3.20E−05 | 0.028397707 |
| CTD-2572N17.1 | −5.965543904 | 0.000118413 | 0.048147308 |
| DLG2 | −1.788845527 | 4.32E−05 | 0.033701311 |
| KIAA1377 | −1.234406774 | 0.000101039 | 0.047137392 |
| SLCO2B1 | 1.68006719 | 0.00010496 | 0.047137392 |
| KRT6B | 3.073204467 | 1.59E−05 | 0.020703369 |
| RP11-1038A11.3 | 6.696361116 | 3.63E−05 | 0.030777674 |
| TBX5 | −3.418397927 | 1.55E−09 | 3.03E−05 |
| TMPRSS12 | 5.92907051 | 0.000111222 | 0.047189497 |
| GUCY1B2 | 4.093777024 | 6.66E−05 | 0.04471402 |
| LINC00426 | 2.188625866 | 4.44E−06 | 0.007323772 |
| RP11-471M2.3 | −9.85296204 | 3.16E−05 | 0.028397707 |
| NOVA1 | −1.412577417 | 1.53E−05 | 0.020703369 |
| RNU6-212P | 5.290013532 | 1.50E−06 | 0.003244996 |
| RP11-297M9.2 | −5.605895376 | 4.50E−06 | 0.007323772 |
| AC087650.1 | 6.237979185 | 2.55E−05 | 0.027597468 |
| ALOX15 | −4.28041122 | 0.000106212 | 0.047137392 |
| COL1A1 | −2.214328008 | 0.000110144 | 0.047189497 |
| CTB-58E17.5 | 4.660563493 | 0.000106269 | 0.047137392 |
| KRT16 | 2.385915598 | 0.000126122 | 0.049063344 |
| KRT17 | 3.469571004 | 5.72E−08 | 0.000558082 |
| RP11-818O24.2 | 3.209071097 | 6.87E−05 | 0.04471402 |
| DLGAP1 | −3.285059431 | 0.000128208 | 0.049063344 |
| LIPG | 2.791315048 | 3.26E−07 | 0.002120648 |
| ZNF677 | −1.790993318 | 7.36E−05 | 0.044888007 |
| CCDC80 | −1.724179635 | 1.06E−06 | 0.002987662 |
| GTF2E1 | 1.677738048 | 0.000130869 | 0.049118529 |
| IGSF10 | −1.82617367 | 5.02E−05 | 0.036647047 |
| LINC01279 | −1.382510312 | 0.000115514 | 0.04796784 |
| RP11-167H9.3 | 7.101392885 | 8.96E−05 | 0.047137392 |
| RP11-225N10.3 | 4.113489784 | 4.06E−05 | 0.032979646 |
| TIMP4 | 3.296871574 | 9.82E−05 | 0.047137392 |
| FSTL5 | −8.57967243 | 1.85E−05 | 0.022581707 |
| SFRP2 | −1.840399088 | 7.23E−05 | 0.044888007 |
| RASGRF2 | −1.294357967 | 8.59E−05 | 0.047137392 |
| SPARC | −1.430078168 | 8.50E−05 | 0.047137392 |
| LAMA4 | −1.014939477 | 5.07E−05 | 0.036647047 |
| ZNF391 | −2.231139803 | 2.95E−05 | 0.028397707 |
| COL1A2 | −1.654053786 | 8.17E−06 | 0.012258238 |
| DPP6 | −3.082561514 | 9.90E−05 | 0.047137392 |
| COL14A1 | −1.94145455 | 4.06E−05 | 0.007323772 |
| RP11-177H2.1 | 6.008407207 | 8.33E−05 | 0.047137392 |
| RP11-363E6.4 | −5.276207375 | 0.000121727 | 0.048484542 |
| SYBU | −1.683870164 | 0.00010079 | 0.047137392 |
| OGN | −1.824901386 | 6.73E−07 | 0.002987662 |
| ABCD1 | 4.773716251 | 1.22E−06 | 0.002987662 |
| CAPN6 | −2.821521038 | 1.05E−06 | 0.002987662 |
| MXRA5 | −1.46183366 | 2.76E−05 | 0.028318761 |

Recognition and/or quantification of the polypeptides described herein (or their precursors) can be used to increase diagnostic confidence in early GVHD, when clinical and microscopic changes may be non-specific but when accurate diagnosis is essential for proper treatment. The polypeptides described herein can be used during acute GVHD to stratify steroid-responsiveness or predict other outcomes (such as the development of chronic GVHD or relapse).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating acute GVHD in a mammal, wherein said method comprises:
   (a) identifying said mammal as having skin cells that express an elevated level of antigen peptide transporter 1, signal transducer and activator of transcription 3, or proteasome subunit alpha type-3 isoform 1, and
   (b) administering a steroid to said mammal under conditions wherein the severity of said acute GVHD within said mammal is reduced.

2. The method of claim 1, wherein said mammal is a human.

3. The method of claim 1, wherein said acute GVHD is acute allo-GVHD.

4. A method for treating acute GVHD in a mammal, wherein said method comprises:
   (a) identifying said mammal as having skin cells that express an elevated level of integrin B2 precursor or LIM domain and actin-binding protein 1, and
   (b) administering a steroid to said mammal under conditions wherein the severity of said acute GVHD within said mammal is reduced.

5. A method for treating acute GVHD in a mammal, wherein said method comprises:
   (a) identifying said mammal as having skin cells that express an elevated level of heat shock protein 105 kDa, hypoxia-induced peptide, or mitochondrial sulfide:quinone oxidoreductase, and
   (b) administering a steroid to said mammal under conditions wherein the severity of said acute GVHD within said mammal is reduced.

6. The method of claim 4, wherein said mammal is a human.

7. The method of claim 4, wherein said acute GVHD is acute allo-GVHD.

8. The method of claim 5, wherein said mammal is a human.

9. The method of claim 5, wherein said acute GVHD is acute allo-GVHD.

* * * * *